(12) United States Patent
Banko

(10) Patent No.: US 11,369,513 B2
(45) Date of Patent: Jun. 28, 2022

(54) LOW-COST DISPOSABLE ULTRASONIC SURGICAL HANDPIECE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 185 days.

(21) Appl. No.: 16/456,843

(22) Filed: Jun. 28, 2019

(65) Prior Publication Data

US 2019/0321067 A1   Oct. 24, 2019
US 2021/0093347 A9   Apr. 1, 2021

Related U.S. Application Data

(63) Continuation-in-part of application No. 16/240,513, filed on Jan. 4, 2019, and a continuation-in-part of
(Continued)

(51) Int. Cl.
*A61B 17/32*   (2006.01)
*A61F 9/007*   (2006.01)
*A61B 17/00*   (2006.01)

(52) U.S. Cl.
CPC .. *A61F 9/00745* (2013.01); *A61B 2017/0023* (2013.01); *A61B 2017/32007* (2017.08);
(Continued)

(58) Field of Classification Search
CPC .............. A61F 9/00745; A61F 9/00736; A61F 9/00754; A61F 9/00763; A61F 9/00772;
(Continued)

(56) References Cited

U.S. PATENT DOCUMENTS 3,906,954 A   9/1975   Baehr et al.
3,976,077 A   8/1976   Kerfoot, Jr.
(Continued)

FOREIGN PATENT DOCUMENTS

CN         106175848 A      6/2016
DE   10 2015 207 150 A1   11/2016
(Continued)

OTHER PUBLICATIONS

International Search Report and Written Opinion in corresponding PCT Application No. PCT/2018/061940, dated Feb. 26, 2019.
(Continued)

*Primary Examiner* — Dianne Dornbusch
(74) *Attorney, Agent, or Firm* — Leason Ellis LLP

(57) ABSTRACT

A disposable ultrasonic handpiece that contains a transducer and a connecting body that is attached to a tube with a cobra work tip at its distal end. The housing that surrounds the ultrasonic transducer does not require waterproofing for repeated autoclaving. Also, the electrical cord that provides power to the transducer is made of very inexpensive wire, along with a low-cost electrical connector. A power cord can be plugged into and unplugged from a socket at the proximal end of the housing and can be reused. Thus, only the housing and its contents need to be disposed of after a procedure, making the disposable part of the handpiece low cost. In addition, the cobra work tip can be provided with a cutting gap that increases its ability to cut.

26 Claims, 8 Drawing Sheets

Related U.S. Application Data application No. 16/001,673, filed on Jun. 6, 2018, now Pat. No. 11,039,955, which is a continuation-in-part of application No. 15/941,366, filed on Mar. 30, 2018, now Pat. No. 11,207,212, which is a continuation-in-part of application No. 15/821,137, filed on Nov. 22, 2017, now Pat. No. 11,207,094.

(52) U.S. Cl.
CPC ............ *A61B 2017/320075* (2017.08); *A61B 2017/320078* (2017.08); *A61B 2017/320082* (2017.08); *A61B 2017/320084* (2013.01); *A61B 2217/007* (2013.01)

(58) Field of Classification Search
CPC .... A61F 9/00781; A61F 9/0079; A61B 17/32; A61B 17/320068; A61B 2017/320069; A61B 2017/32007; A61B 2017/320071; A61B 2017/320072; A61B 2017/320073; A61B 2017/320074; A61B 2017/320075; A61B 2017/320077; A61B 2017/320078; A61B 2017/320082; A61B 2017/320084; A61B 2017/320088; A61B 2017/320089; A61M 1/77; A61M 1/774
See application file for complete search history.

(56) References Cited

U.S. PATENT DOCUMENTS

| | | | |
|---|---|---|---|
| 3,990,452 | A | 11/1976 | Murry et al. |
| 4,168,447 | A | 9/1979 | Bussiere et al. |
| 4,320,761 | A | 3/1982 | Haddad |
| 4,504,264 | A | 3/1985 | Kelman |
| 4,634,420 | A * | 1/1987 | Spinosa ............ A61F 9/00745 433/119 |
| 4,793,345 | A * | 12/1988 | Lehmer ............ A61F 9/00745 606/107 |
| 5,151,083 | A * | 9/1992 | Pichler ........... A61B 17/320068 604/22 |
| 5,359,996 | A | 11/1994 | Hood |
| 5,486,162 | A * | 1/1996 | Brumbach ......... A61F 9/00745 604/22 |
| 5,591,184 | A * | 1/1997 | McDonnell ....... A61B 17/3203 604/22 |
| 5,667,489 | A * | 9/1997 | Kraff ................ A61F 9/00745 604/22 |
| 5,693,062 | A | 12/1997 | Stegmann et al. |
| 5,843,109 | A * | 12/1998 | Mehta ................ B06B 1/0618 606/169 |
| 6,165,150 | A * | 12/2000 | Banko ................ A61F 9/00745 604/22 |
| 6,214,017 | B1 | 4/2001 | Stoddard et al. |
| 6,454,763 | B1 * | 9/2002 | Motter ............... A61F 9/00802 606/15 |
| 6,478,781 | B1 * | 11/2002 | Urich ................. A61M 1/0058 604/264 |
| 6,592,541 | B1 | 7/2003 | Kurwa |
| 7,083,589 | B2 | 8/2006 | Banko et al. |
| 8,348,967 | B2 | 1/2013 | Stulen |
| 8,641,658 | B1 | 2/2014 | Banko |
| 2002/0007200 | A1 | 1/2002 | Desinger |
| 2002/0111608 | A1 * | 8/2002 | Baerveldt ........... A61F 9/00745 606/6 |
| 2002/0161326 | A1 * | 10/2002 | Sussman ........... A61F 9/00736 604/35 |
| 2003/0212332 | A1 | 11/2003 | Fenton et al. |
| 2003/0229344 | A1 | 12/2003 | Dycus et al. |
| 2006/0058811 | A1 * | 3/2006 | Kishimoto ......... A61F 9/00736 606/107 |
| 2007/0060926 | A1 | 3/2007 | Escaf |
| 2008/0234710 | A1 | 9/2008 | Neurohr et al. |
| 2009/0082716 | A1 | 3/2009 | Akahosi |
| 2010/0160852 | A1 * | 6/2010 | Moore, Jr. ............ B06B 1/0269 604/22 |
| 2010/0168741 | A1 * | 7/2010 | Sanai .................. A61B 18/148 606/42 |
| 2011/0160620 | A1 * | 6/2011 | Gill ................ A61B 17/320068 601/2 |
| 2011/0196399 | A1 | 8/2011 | Robertson et al. |
| 2014/0163595 | A1 | 6/2014 | Witt et al. |
| 2014/0276364 | A1 | 9/2014 | Sussman |
| 2014/0029269 | A1 | 11/2014 | Adey et al. |
| 2015/0025451 | A1 | 1/2015 | Banko |
| 2015/0045806 | A1 * | 2/2015 | Urich ................ A61F 9/00745 606/107 |
| 2015/0126994 | A1 | 5/2015 | Matsui et al. |
| 2016/0374707 | A1 | 12/2016 | Akagane |
| 2019/0133823 | A1 | 5/2019 | Banko |

FOREIGN PATENT DOCUMENTS

| | | |
|---|---|---|
| EP | 2521509 B1 | 1/2011 |
| WO | WO 2008/118709 A1 | 10/2008 |

OTHER PUBLICATIONS

International Search Report and Written Opinion in corresponding PCT Application No. PCT/US2019/024910, dated Jun. 24, 2019.
International Search Report and Written Opinion in corresponding PCT Application No. PCT/US2019/035747, dated Nov. 25, 2019.
International Preliminary Report on Patentability in corresponding PCT Application No. PCT/US2018/061940, dated Jun. 4, 2020.
Non-Final Office Action in corresponding U.S. Appl. No. 15/821,137, dated Jun. 24, 2020.
International Preliminary Report on Patentability in corresponding PCT Application No. PCT/US2019/035747, dated Dec. 8, 2020.

* cited by examiner

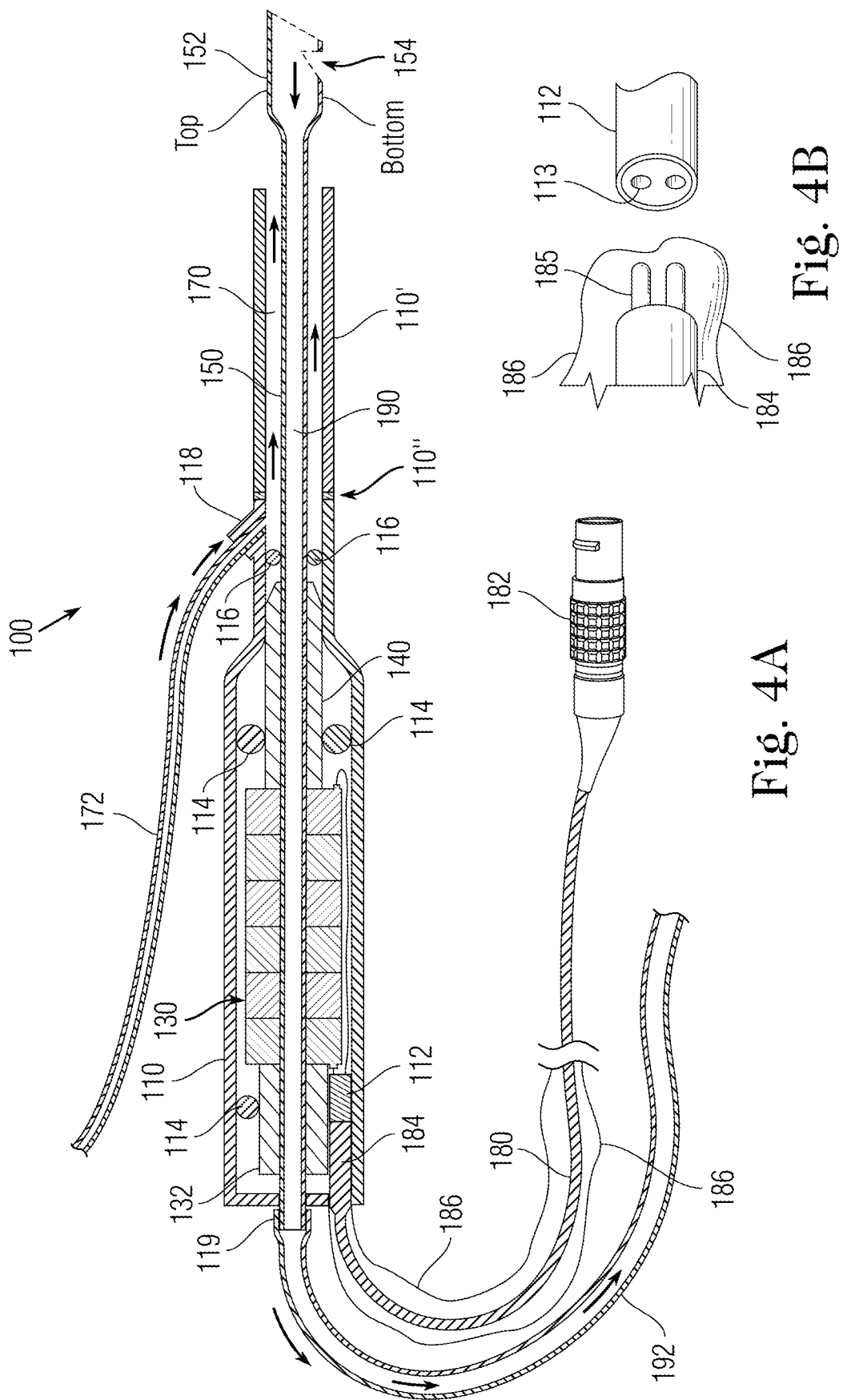

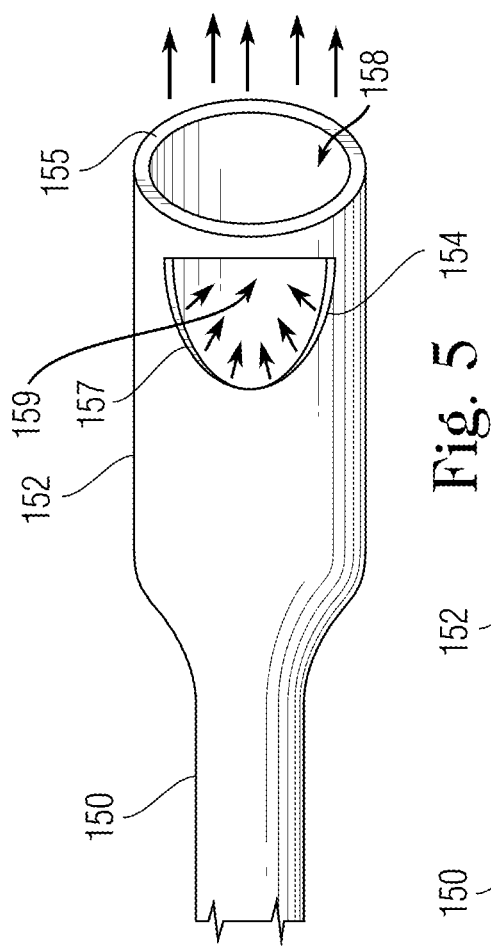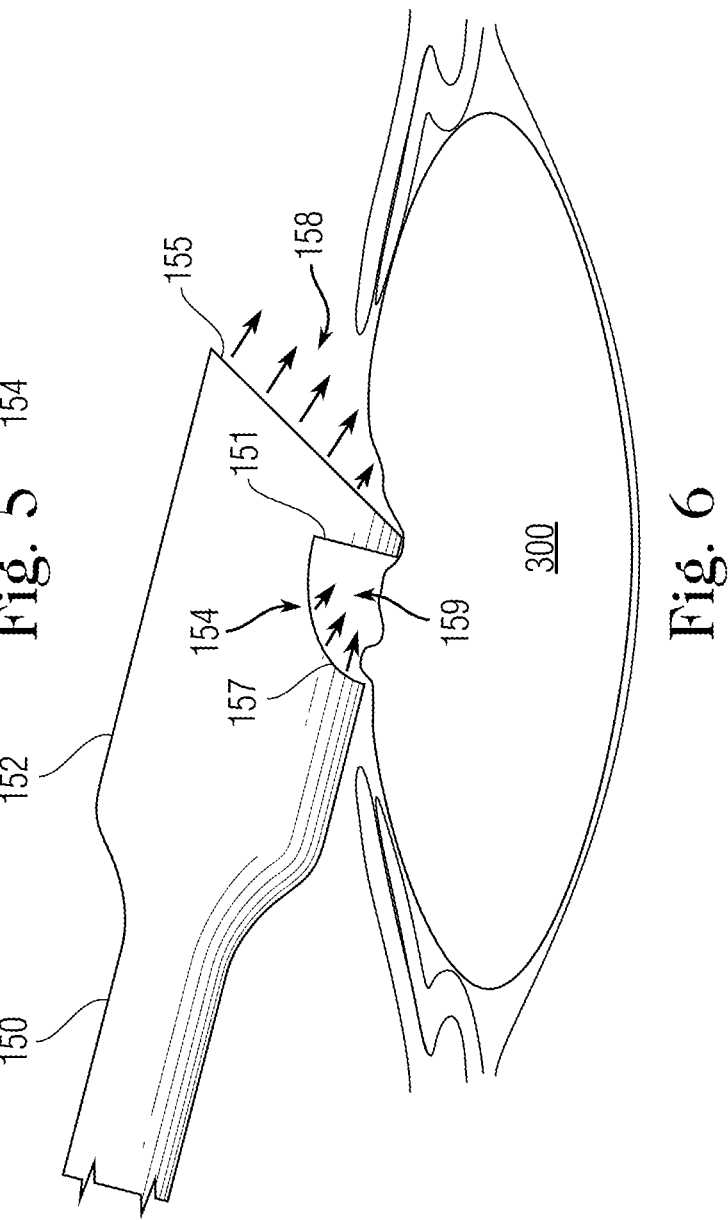

LOW-COST DISPOSABLE ULTRASONIC SURGICAL HANDPIECE

The present invention is a continuation-in-part of (a) U.S. patent application Ser. No. 16/240,513 filed Jan. 4, 2019, which in turn is a continuation-in-part of U.S. patent application Ser. No. 16/001,673 filed Jun. 6, 2018, and is also a continuation-in-part of (b) U.S. patent application Ser. No. 15/941,366 filed Mar. 30, 2018, which in turn is a continuation-in-part of U.S. patent application Ser. No. 15/821,137 filed Nov. 22, 2017; the contents of all of which are incorporated herein by reference in their entirety.

TECHNICAL FIELD

The present invention is generally directed to surgical handpieces, particularly disposable ultrasonic surgical handpieces for the removal of cataracts from the eye of a patient by phacoemulsification.

BACKGROUND OF THE INVENTION

The use of ultrasonic surgical instruments for various surgical procedures, including cataract removal, is well known. For example, the phacoemulsification procedure, first disclosed in U.S. Pat. No. 3,589,363 of Anton Banko and Charles D. Kelman, which issued on Jun. 29, 1971, recently reached its 50-year anniversary.

Phacoemulsification handpieces today are essentially the same as the ones developed in the 1970s. They have a very complicated design, are expensive to manufacture, and require sterilization by autoclaving in order to reuse them. The main reason for these disadvantages is the fact that the irrigation and aspiration lines extend through the handpiece and interfere with the performance of the vibrating transducer in the handpiece.

Additionally, the housing that contains the vibrating transducer must be waterproof in order to withstand the high temperatures and pressures of the pressurized steam used during autoclaving. The power cord and the electrical connector must also be able to withstand these high temperatures and pressures of the pressurized steam and must be water proof because they also must be sterilized. This adds considerable expense to the materials and procedures used in the manufacture of the handpiece.

Due to the complexity of the handpieces and the expense of the manufacturing process, ultrasonic phacoemulsification handpieces are generally sold to ophthalmic surgeons with a price ranging from four thousand to seven thousand dollars each. For example, the Alcon® OZil® Torsional Handpiece (Alcon® Model 8065750469) currently retails for $7,492.95 from Medex Supply.

FIG. 1 shows a prior art handpiece 600 made by Surgical Design Company, the present applicant, with a magnetostrictive ultrasonic transducer 630 that works by expanding and contracting nickel laminations 610 in a magnetic field. The magnetic field is provided by a wire coil 620 that is wound within the handpiece. As the nickel laminations expand and contract, the ultrasonic vibration is amplified and transmitted through a connecting body 640 to the work tip 650 through the connecting body 640. This version of the handpiece contains fluid lines 670, 690 within the vibrating transducer. The center fluid line 690 is the aspiration line that starts with the vibrating hollow phacoemulsification needle work tip 650 and ends at the rear fluid connector 660 of the handpiece. Similarly, the irrigation line 670 enters the rear connector 660 and goes through the nickel laminations 610. From there, the irrigation line enters the irrigation sleeve 680.

FIG. 1 illustrates the complexity of the handpiece 600. This complexity is due to the design of the handpiece, the autoclaving requirements, and the dozens of specialized components that are required to construct the handpiece.

FIG. 2 shows an enlarged view of the prior art connecting body 640 for the same handpiece 600. The aspiration line 690, the irrigation line 670, and a thread design 700 where the connecting part 640 attaches to the work tip 650 are shown. FIG. 2 illustrates the complexity and tolerances of the machining required to manufacture a titanium connecting body. This complexity is in part due to the existence of the fluid lines in the body of the handpiece. For example, the tolerances and the radii are specified to thousandths of an inch.

FIG. 3 shows a typical prior art design for the coil assembly 700 for the same handpiece 600, including the wire coil 620. This portion of the handpiece has center fluid line 690 and irrigation line 670 passing through it. Further, this portion can be seen in relation to the rear fluid connector 660, an O-Ring 710 for confining fluid to the lines, a waterproof housing 720 that surrounds the structure, a coil nut 730 that holds the wire coil 620 in place and a centering pin 740. Also, as shown in FIG. 3 there is a cable connector 750, a power cord 790, a power cord jacket 760, a socket set screw 770 and soldering terminals 780 that allow the ultrasonic signal transmitted over cable 790 to be applied to the coil to create the magnetic field that vibrates the laminations 610, the connecting body and the work tip.

Repeated autoclave cycles require extraordinary efforts to seal the handpiece so that it can withstand the moisture, high pressure, and high temperatures of the autoclaving cycle. For example, in the prior Surgical Design product and other prior products the coil wire 620 is wound onto the handpiece and sealed with an epoxy such as the Huntsman Araldite® CY 8043 Resin Brominated Epoxy. The power cord jacket 760 and the soldering terminals 780 that connect the power cord 790 to the wire coil 620 are sealed with GE RTV133 silicone rubber adhesive sealant that can withstand autoclaving. The power cord 790 is prone to failures from repeated autoclaving because the high pressures and temperatures result in water vapor that gets inside the insulation and corrodes the wires. To minimize corrosion, custom-made power cords need to be used in the handpiece. For example, a nickel-plated wire with a gold coating can be used, which is available from New England Wire Technologies (Lisbon, N.H. 03585). A roll of this custom wire was offered for $28,882.45 per 1000 ft in 2007, but this product is no longer available because of the complexity and cost of manufacturing it.

Because of the expense involved in the manufacture of ultrasonic surgical handpieces, it has so far been impractical to offer them as disposable items. Manufacturers have only offered reusable, autoclavable handpieces.

One of the most common uses for ultrasonic handpieces is in the field of ophthalmology is for removing cataracts. Phacoemulsification systems have typically been sold in combination with the console that contains the ultrasonic generator and controls the fluidics. The titanium phacoemulsification tips and external plastic tubing that transports fluid between the surgical system and the handpiece are marketed as disposable, with the rationale that because these components come into contact with the patient's bodily fluids, it is easier and safer to dispose of them after a single use rather than autoclave them. This approach has been very profitable for manufacturers. However, the present inventor has realized that logically this does not make sense since the handpiece itself is being reused after exposure to bodily fluids, even though the channels internal to the handpiece (especially the aspiration tube) are exposed to bodily fluids and are much harder to clean and sterilize.

Concerns about the spread of infection through contaminated body fluids have intensified significantly in recent years with the escalation of HIV/AIDS and other lethal viruses; antibiotic-resistant bacteria; Toxic Anterior Segment Syndrome (TASS); and Prion (Mad Cow) Disease, against which autoclaving may not be 100% effective. For example, with Prion Disease, the proteins are very stable and normal autoclaving may not be enough to denature the structure of the infectious protein and render it harmless. Also, regarding TASS, the Association of periOperative Registered Nurses (Denver, Colo. 80231) reports that > most cases . . . appear to result from inadequate instrument cleaning and sterilization. Other reported TASS cases were associated with glutaraldehyde and detergent residue on instruments, endotoxins from gram-negative bacteria in ultrasonic cleaners, impurities in steam from improperly maintained sterilizers, and degradation of brass surgical instruments sterilized by hydrogen peroxide gas plasma. Prevention of TASS requires thorough cleaning and rinsing of surgical instruments.
> 
> ("Recommended Practices for Cleaning and Care of Surgical Instruments and Powered Equipment," Association of periOperative Registered Nurses, p. 24) Thorough cleaning does not always occur.

Even when it is effective, the autoclaving process is time-consuming and expensive. The Association of Surgical Technologists (Littleton, Colo. 80120) details 15 practices over 30 pages regarding the complexity of dealing with the decontamination of surgical instruments ("Standards of Practice for the Decontamination of Surgical Instruments," Association of Surgical Technologists, which is incorporated herein by reference in its entirety). These practices involve several different steps and techniques such as placing instruments in a sterile water bath directly after surgery; manually rinsing and flushing the instruments; using ultrasonic cleaning baths with or without enzymatic detergents; etc.

The "Guidelines for the Cleaning and Sterilization of Intraocular Surgical Instruments," compiled by the Ophthalmic Instrument Cleaning and Sterilization (OICS) Task Force (which includes representatives from the American Society of Cataract and Refractive Surgery (ASCRS), the American Academy of Ophthalmology (AAO), and the Outpatient Ophthalmic Surgery Society (OOSS)) gives an overview of the comprehensive training required of nursing and medical staff regarding sterilization procedures. The guidelines, which is incorporated herein by reference in its entirety, recommend that > "Personnel . . . should be properly trained in handling, cleaning, and sterilizing intraocular surgical instruments and subject to periodic oversight. In addition to the general principles of asepsis, this training should also include the cleaning, inspection, preparation, packaging, sterilization, storage, and distribution of intraocular surgical instruments. Appropriate staff should also be trained in related tasks, such as equipment operation and preventive maintenance. They should undergo competency validations by direct observation of performance. Staff education, training, and validation of competency should be updated and documented at least annually and be coincident with the introduction of new surgical equipment, medical devices, or packaging systems."

In addition, each instrument comes with its own specifications for autoclaving from the manufacturer, but it is highly impractical to autoclave instruments individually. All of these procedures require strict quality control guidelines and specifications, as well as careful documentation, and this takes up a significant amount of time.

SUMMARY OF THE INVENTION

In accordance with the invention an ultrasonic surgical handpiece is provided with a so called "cobra" cone shaped work tip located at the distal end of the connecting body of handpiece. The connecting body and the work tip may be manufactured as one piece or in two pieces that are connected together. In a preferred embodiment the connecting body and work tip are made in one piece. As a result, there is no thread between the connecting body and the work tip. This cuts down on manufacturing expense, greatly improves the transmission of ultrasonic vibrational energy from the connecting body to the work tip and is easier to keep clean because there are no threads to provide spaces for bacteria. The increase in efficiency allows for smaller, less expensive parts to be used to achieve the same output energy for removing surgical tissue, e.g., cataracts, than a typical more complex handpiece. Because of the reduction in cost, the connecting body/work tip can be disposable after each use. Since the aspiration channel passes through both the work tip and handpiece, this construction also eliminates the need to sterilize them between uses, thus saving further costs and speeding up the process when multiple patients are operated on during a single session.

The ultrasonic surgical handpiece has a housing that surrounds the ultrasonic vibration generating elements and the connecting piece, and extends along the work tip to the vicinity of the cobra cone shape, thus forming an aspiration sleeve. This housing, unlike the prior art, is not designed, manufactured, or extensively sealed to be waterproof in order to withstand numerous autoclaving sterilization cycles because, being disposable, there is no need to autoclave it. Further, the disposable aspect of the handpiece also allows the power cord and connector to be made of simpler, less expensive materials.

Ultrasonic surgical handpieces have always been complex and expensive to manufacture. For example, phacoemulsification handpieces used for removing cataracts have the irrigation and aspiration fluid lines built into the handpiece. This interferes with the core vibrating transducer within the handpiece, and results in unnecessary complexity. Furthermore, the autoclaving of these handpieces and materials management is a huge disadvantage to the operating room staff. This complexity and its cost are avoided in part with the present invention wherein the irrigation fluid lines do not pass through the ultrasonic generating parts and the connecting part. Instead, the irrigation line connects to the housing beyond the connecting piece and can be made to be disposable. Besides, eliminating the irrigation line from the ultrasonic generating parts and the connecting part simplifies the design and reduces its cost.

The electrical power cord and connector that supply electricity to the ultrasonic vibrating parts are made detachable from the hand piece. Since no bodily tissue or fluids contact the cord and connector, it could be asserted that it need not be disposable and can be reused. However, the cable plug does contact the handpiece, even if it does not contact bodily tissue or fluids. Thus, under strict protocol, it enters the sterile field and should not be reused. This can be overcome, however, by surrounding the plug with a sterile sheet so it can be reused. Nevertheless, the rest of the hand piece is intended to be disposed after each use. In particular, the aspiration line and the housing with its ultrasonic vibration generating parts, connecting body and work tip, are thrown away after each use. The irrigation line can be made detachable from the housing and reused, or it can also be thrown away. Because the disposable parts are of a simpler design and are not extensively sealed to be waterproof in order to withstand numerous autoclaving cycles, their manufacture is simpler with less expensive materials, so the overall cost is greatly reduced. Further, the connection of the power cord to the ultrasonic vibration parts can also be made simpler and with less expensive materials because corrosion of the wires due to autoclaving is not a concern. This represents another basis for reducing cost whether the cord is reused or disposed of after use.

The benefits of having an entirely disposable ultrasonic surgical handpiece are numerous. As the European Pharmaceutical Review (Kent, TN16 1NU, UK) explains in general: "The advantages of single-use technology can be summarized as: eliminating the need for cleaning; removing requirements for in-house sterilization (typically by autoclaving) for all components; reducing the use of cleaning chemicals; cutting storage requirements; lowering process downtime; and increasing process flexibility and reducing cross-contamination risks." (Dr. Tim Sandle, "Strategy for the adoption of single-use technology," 22 Mar. 2018, which is incorporated herein by reference in its entirety.)

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 4A is a cross-section of a completely disposable ultrasonic surgical handpiece with a cobra work tip, external irrigation fluid tubes, a piezoelectric crystal transducer and a detachable electrical cord according to the present invention, while FIG. 4B is an enlarged view of a plug at the end of the cord, a sterile sheet and a socket in the housing prior to being connected to each other;

FIG. 5 is bottom view of the cobra work tip showing a secondary semicircular cutting gap wherein the major portion of the gap is toward the distal end of the work tip and illustrating the direction of ultrasonic forces from the work tip;

FIG. 6 is a side view of the cobra work tip of FIG. 5 with the secondary cutting gap of FIG. 5 engaging a cataract in the eye of a patient;

DETAILED DESCRIPTION OF THE INVENTION

Figure 1:
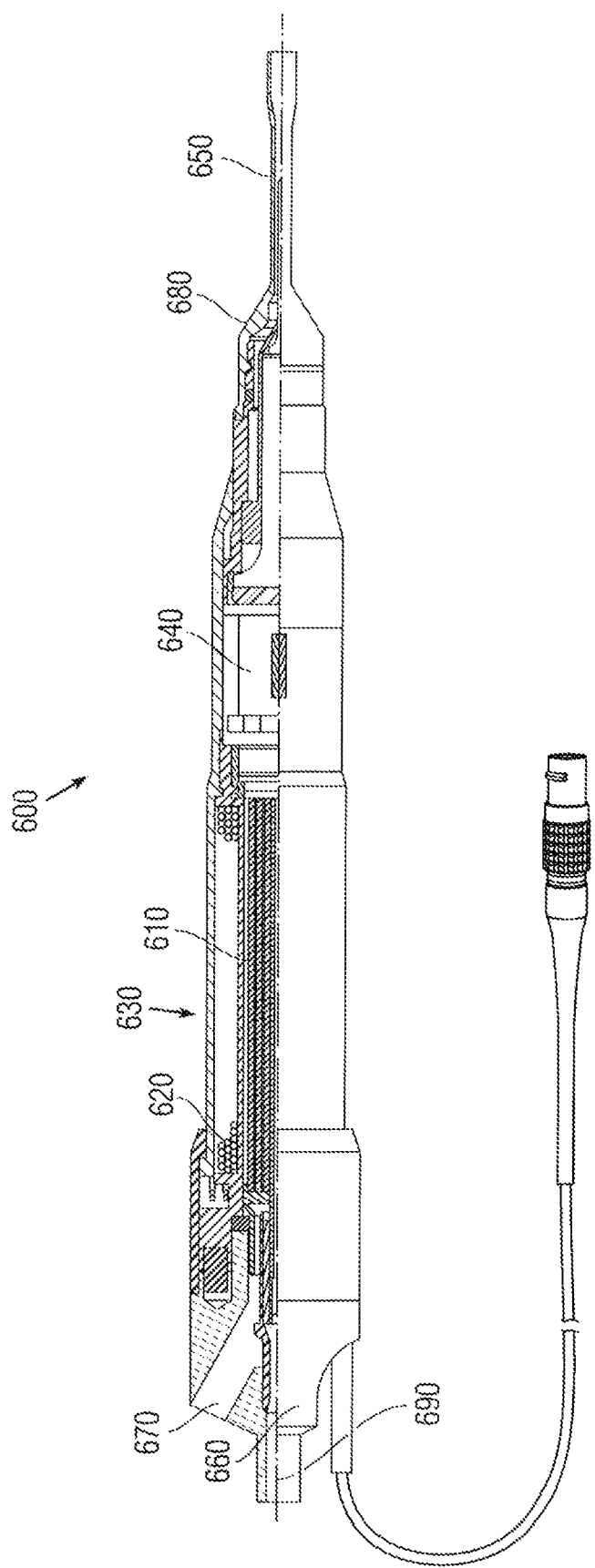
FIG. 1 is a view in partial cross-section of a prior art ultrasonic surgical handpiece.

FIG. 4A shows a disposable ultrasonic surgical handpiece 100 according to the present invention. This handpiece is unique in its design simplicity. The handpiece has a housing 110 that can be made of plastic, metal or rigid paper, and does not require waterproofing to withstand the moisture, high temperatures, and high pressures of autoclaving. The housing has a larger diameter portion at its proximal end to accommodate internal element and it necks down to a reduced diameter portion toward its distal end. The reduced diameter portion extends to a distal portion or sleeve 110' at its distal end that extends to the vicinity of a work tip of the handpiece. The internal elements can be fixed to the housing 110 with simple plastic or elastic components 114, e.g., O-rings. No epoxies or sealants are required between the housing 110 and the internal components. The power cord socket 112 and its connector 184 also do not require epoxies or silicones to keep moisture from entering the rear of the handpiece. In addition, the power cord 180 can be made of simple, inexpensive electrically conducting wires covered with insulation, where the insulation is only required for the purpose of isolating the electrical conductivity of the wires. It is not necessary to insulate the wires against corrosion due to moisture, high temperatures, and detergents or other chemicals that are encountered during autoclaving.

The ultrasonic transducer 130 of this handpiece 100 can be either magnetostrictive or made of ceramic piezo crystals. A connecting body 140 extends from the transducer 130 and surrounds a long tube 150 with a cobra work tip 152 at its distal end. The long tube 150, which may be one piece or a series of connected pieces, runs through the transducer 130 to a connector 119 at the proximal end of the housing 110. The transducer 130 with an extension 132 and the connecting body 140 are supported in the housing 110 by the O-rings 114. The long tube 150 is supported in the housing by smaller O-rings 116.

Figure 2:
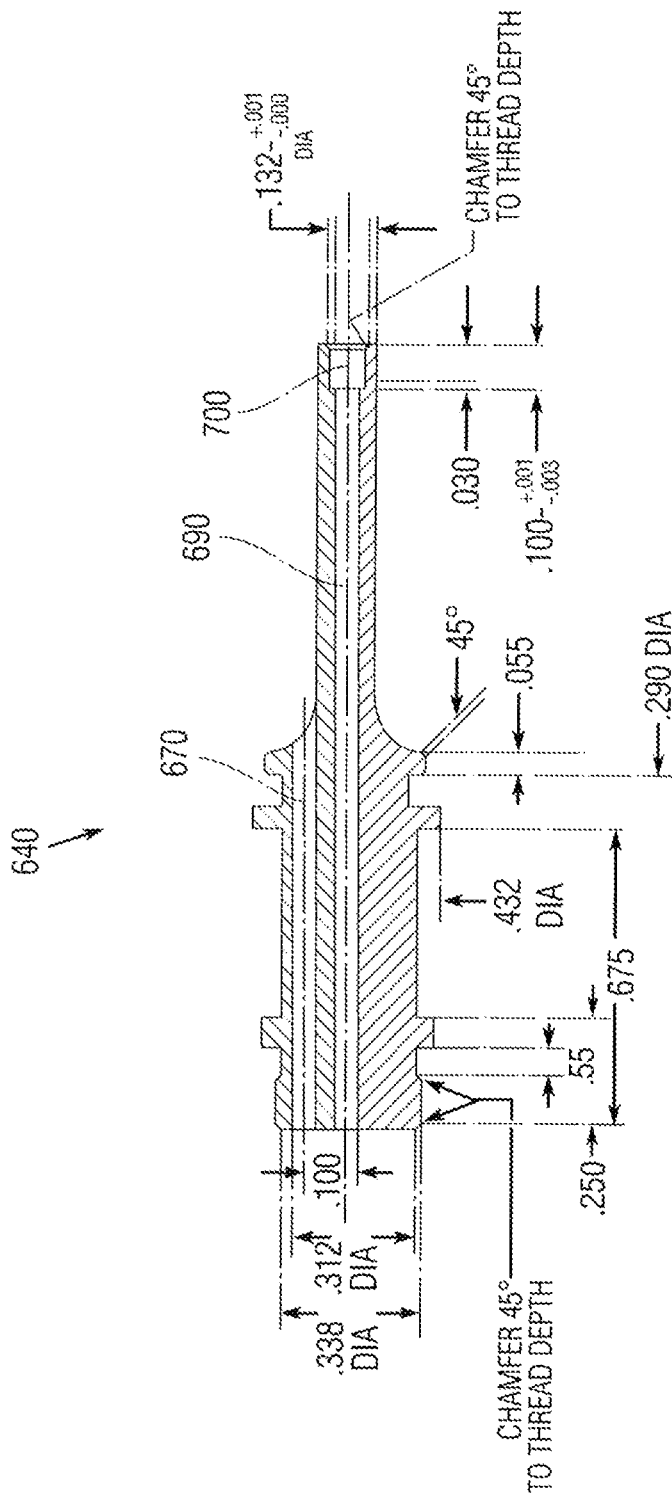
FIG. 2 is a detailed enlarged cross-sectional view with dimensions of a prior art ultrasonic connecting body that is a component of FIG. 1.

The distal end of the housing or a separate sleeve 110' surrounds the long tube and extends to the vicinity of the cobra work tip 152, thus forming an irrigation channel 170. The distal end 110' of the housing 110 may actually be made of a flexible silicone material which forms the outer sleeve of the irrigation channel 170. Having this part made of flexible silicone makes it easier to insert into an incision in the eye. A part 110" connects the main housing 110, which would be rigid, to the flexible sleeve 110'. A connector 118 at the distal end of the main housing 110 allows an irrigation line 172 to connect to the irrigation channel 170. A channel 190 through the cobra tip 152, long tube 150 to the proximal end of the handpiece forms the aspiration channel that is connected to aspiration tube 192. In one embodiment main housing 110 is made of a rigid material and distal housing 110' is made of a flexible silicone material. In another embodiment all of the housing is made of flexible material (e.g., silicone), but the part 110 is reinforced, e.g., with an epoxy resin, paper, plastic, etc. to make it rigid Having the connecting body 140, the tube 150 and the work tip 152 as a single piece has several significant advantages. Manufacturing a single-piece (e.g., by casting, 3D printing, etc.) costs only a fraction of the cost of manufacturing a connecting body, tube and work tip as separate pieces with threads that screw them together. For example, creating the thread 700 in FIG. 2 requires precision machining with extremely tight tolerances (thousandths of an inch). In addition to the expense, unless the thread on the work tip exactly matches the thread on the connecting body, there is a loss of ultrasonic energy between the transducer 130 and the work tip 152. In particular, there is never one-hundred percent efficiency in coupling the parts, so there is a power loss especially during ultrasonic vibration when the connecting body transmits the vibration at a frequency of anywhere from 44 kHz/s to 50 kHz/s. An arrangement in which the connecting body and work tip are a single piece is thus much more efficient for transmitting ultrasonic vibration and offers cost-savings that are so significant that the handpiece can be disposable. If tube 150 is in one piece, the handpiece can be constructed from the tube outward. In which case the main housing including the reduced diameter (necked down) portion may be made in two axial half shells that are placed about the transducer with tube 150 and connecting piece 140. The halves are brought together and sealed.

The cobra tip 152 has the conventional cone shape of such devices. However, it may also have a cutting gap 154 at the bottom edge as shown in FIG. 4A. This gap gives the cobra tip additional cutting capability as will be explained below.

Figure 3:
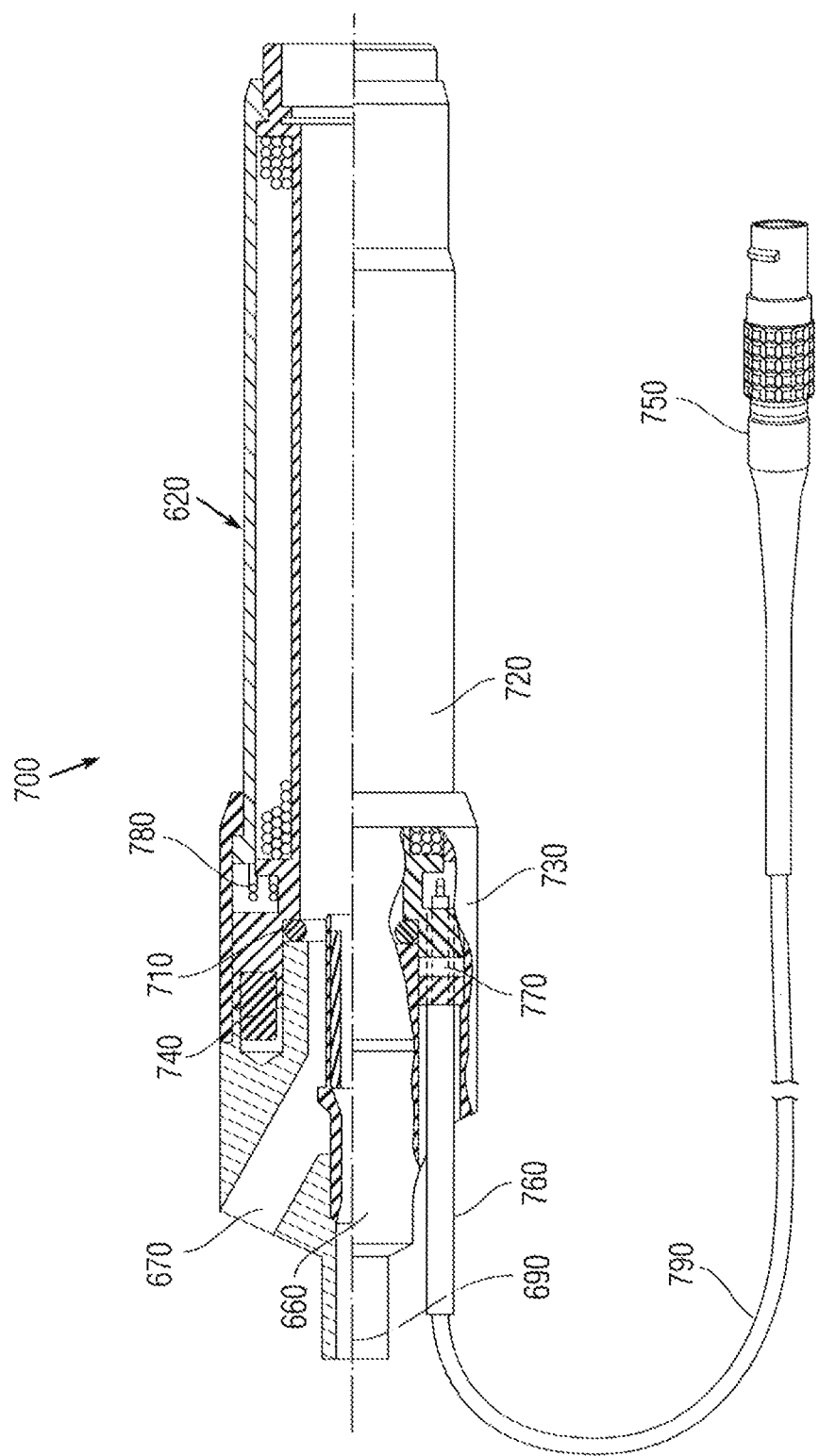
FIG. 3 is a partial cross-section of prior art ultrasonic surgical handpiece that details the coil assembly of FIG. 1.

Power is provided to the handpiece via power cord 180. A connector 182 of the power cord is attached to a console (now shown) that contains an ultrasonic signal generator and also controls the fluidics. The ultrasonic signal is passed from connector 182 through cord 180 to plug 184 on the proximal end of the ultrasonic surgical handpiece 100. Plug 184 is detachably connected to socket 112 in the housing, which is permanently electrically connected to the transducer 130. In one embodiment the power cord parts differ from similar parts 750 and 790 of the prior art as shown in FIG. 3, in that they are made disposable, because they never have to withstand autoclaving. In particular, they need not be waterproof or corrosion resistant, and as a result can be less expensive than the prior art.

Sterilization protocols differ in different parts of the world. Thus, depending on local medical protocols, it may be deemed that because the power cord will not come into contact with bodily fluids or tissue during a procedure, there is no need to dispose of the cord. Instead, when a procedure is completed, the cord can be disconnected from the used hand piece and connected to a fresh hand piece for the next procedure. This not only results in material cost savings, but it reduces the time required to start a new procedure since the plug 182 does not have to be removed from the console.

The cable plug does contact the handpiece, even if it does not contact bodily tissue or fluids. Thus, under strict healthcare protocols, it enters the sterile field and should not be reused. This can be overcome, however, by surrounding the plug with a sterile sheet so it can be reused. In order to overcome this problem a sterile sheet can be interposed between the plug of the cord and the socket of the housing. FIG. 4B is an enlarged view of the plug 184 and the socket 112 at the left end of the handpiece before they are connected. Sterile sheet 186 is placed between these parts.

When plug 184 is connected to socket 112 its pins 185 pierce the sheet and enter openings 113 in the socket 112. In this way the cord 180 is isolated from the sterile operating field in which the handpiece exists. In this embodiment, before the handpiece is discarded the plug 184 is disconnected from the socket. By placing a new sterile sheet over the plug 184, the cord 180 can be used with a new handpiece without having to sterilize it. At some point, however, it may be advisable to have the cord and a batch of others sterilized, perhaps by a professional using non-liquid means. In such a situation, it may be economical to make the cord water proof, so it can be sterilized after a number of uses.

During a typical phacoemulsification procedure an incision is made in the eye, and the surgeon extends the work tip 152 through the incision and into the vicinity of a cataract that is to be removed. The console is then operated so that irrigation fluid is directed into the incision through a tube 172, a connector 118 in the reduced diameter portion of housing 110 and into a channel 170 formed by the space between the interior of housing sleeve 110' and the exterior of the tube 150. Similarly, fluid and cataract tissue are withdrawn from the incision through a channel 190 in the work tip 152, long tube 150 and flexible tube 192. For example, irrigation fluid from the console may be passed through flexible plastic tube 172 attached to the console and a connector 118 on the housing 110 that leads to channel 170. Fluid may be aspirated from the incision through the cobra tip 152, long tube 150 and flexible plastic tube 192 connected to tube 150 by a connector 119 for delivery back to the console or a separate disposable container (not shown). Tube 172 may extend to a rotary peristaltic pump on the exterior of the console, as opposed to entering into the console itself.

When a cataract 300 is contacted with the work tip 152 as shown in FIG. 6, the console provides ultrasonic electrical signals through cable 180 to the transducer 130, which causes the tip 152 to vibrate at an ultrasonic frequency and to chop or emulsify the cataract tissue. During this procedure the surgical site is bathed in irrigation fluid from channel 170 (FIG. 4) and the pieces of cataract are withdrawn with the aspiration fluid through channel 190. In this operation bodily fluid is entrained with the aspiration fluid. It has been discovered that the vibration of tube 150 is amplified by the cone shape of the cobra tip so that enhanced cutting is achieved with the leading edge 155 of the tip as shown in FIGS. 5 and 6. It is this edge that plays the major roll in breaking up the cataract, i.e., where the edge contacts the cataract.

In the design for the cobra tip according to the present invention the edge 155 is slanted from front to back as shown in FIG. 6. Defining the location of the most proximal area of this edge as the "bottom" of the tip, it can be seen in the embodiment of FIGS. 4A, 5 and 6 that the cutting gap 154 is located at the bottom. As the cobra tip is vibrated at ultrasonic frequencies, the edge 155 provides cutting force as illustrated by the arrows. In addition, the proximal edges 157 of cutting gap 154 also provide supplemental cutting force during a forward vibration stroke as shown by the arrows. Because a surgeon will typically angle the work tip, so the bottom portion of the edge contacts the cataract tissue, the proximal edge 157 of gap 154 is also brought into contact with the cataract tissue to provide additional cutting to break up the cataract. Because aspiration force is applied through the cobra tip, as pieces of cataract tissue is broken off by edge 155, they are sucked into the work tip main opening 158 surrounded by edge 155. In like manner, as pieces are broken off by edge 154, they are sucked into the work tip through the supplemental opening 159 surrounded by the edge 157.

A distal edge 151 of the gap 154 also provides a cutting force during the backward vibration stroke of the work tip. Such cutting force is not provided by the edge 155 so the gap 154 provides further cutting ability during the back stroke.

The cobra work tip 152 shown in FIGS. 4-6 has a cutting gap 154 with a semicircular shape in its bottom view. In its side view the distal edge 151 of the gap is perpendicular to the outer surface and the rest falls along an arc that extends in the proximal direction somewhat in the shape of a quarter circle. The portion of the arc shaped edge that reaches the outer surface is the portion that engages in cutting the cataract during the forward stroke of the work tip, while edge 151 engages in cutting the cataract during the rearward stroke.

Figure 7B:
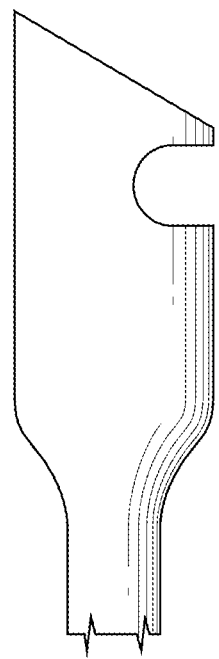
FIGS. 7A and 7B are a bottom view and a side view, respectively, of a cobra work tip with a semicircular cutting gap wherein the major portion of the gap is toward the proximal end of the work tip.
Figure 7A:
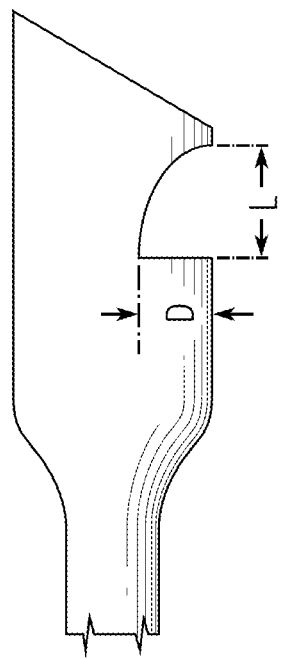

FIGS. 7A and 7B illustrate a bottom view and a side view, respectively, of a cobra work tip with a different semicircular cutting gap. In the embodiment the proximal edge of the gap is perpendicular to the outer surface and extends for a distance D and the rest of the edge falls along an arc that extends in the distal direction for a distance L somewhat in the shape of a quarter circle. In this embodiment the perpendicular edge that reaches the outer surface is the portion that engages in cutting the cataract during the forward stroke. The cutting gap 154 thus extends both perpendicular to the axial direction by the distance D and in the axial direction of the cobra tip by the distance L sufficient for an edge of the gap to engage tissue. In a typical embodiment values for D are between 0.008 and 0.012 inches, while typical values for L are between 0.12 and 0.24 inches.

As shown in U.S. Pat. No. 6,159,175 of Strukel et al., is has been known to place aspiration holes in the side walls of cobra work tips. However, in those cases there is no or a relatively small distance D so that these holes do not provide cutting edges.

Figure 8B:
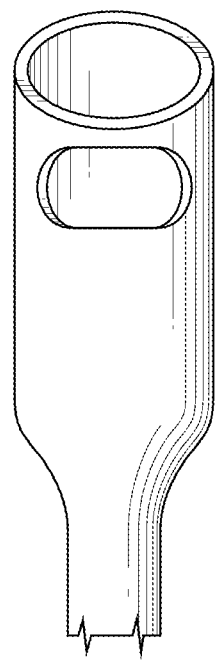
FIGS. 8A and 8B are a bottom view and a side view, respectively, of a cobra work tip with an oval cutting gap.
Figure 8A:
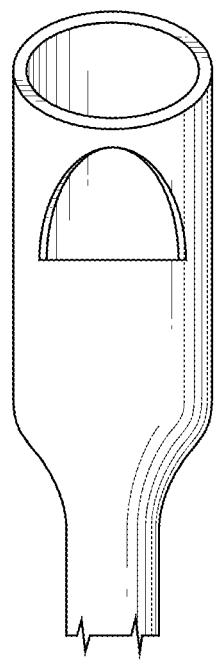

FIGS. 8A and 8B are a bottom view and a side view, respectively, of a cobra work tip with an oval cutting gap. As shown in FIG. 8B the shape from the side is in the form of an inverted U shape.

Figure 9B:
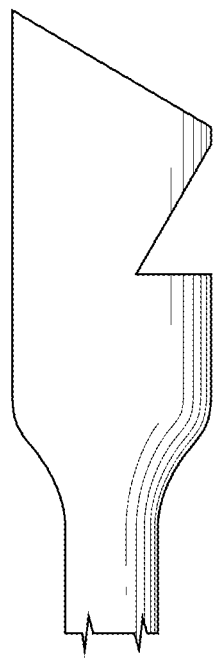
FIGS. 9A and 9B are a bottom view and a side view, respectively, of a cobra work tip with a triangular cutting gap wherein the major portion of the gap is toward the proximal end of the work tip.
Figure 9A:
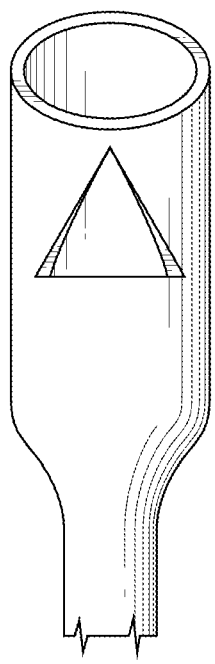
Figure 10A:
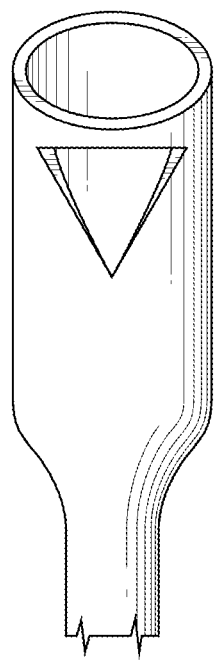

FIGS. 9A and 9B are a bottom view and a side view, respectively, of a cobra work tip with a triangular cutting gap. As shown in FIG. 9B the shape of the distal edge of the gap is perpendicular to the outer surface and the rest falls along a straight line that extends in the proximal direction toward the outer surface. The portion of the edge that reaches the outer surface at the proximal location in FIG. 9B would typically engage in cutting the cataract.

Figure 10B:
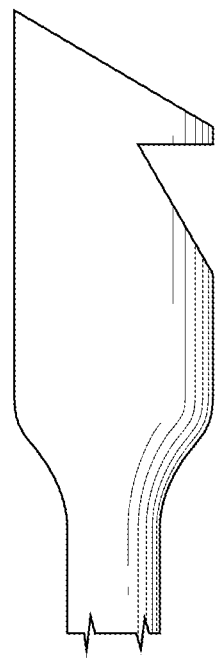
FIGS. 10A and 10B are a bottom view and a side view, respectively, of a cobra work tip with a triangular cutting gap wherein the major portion of the gap is toward the distal end of the work tip.
Figure 11B:
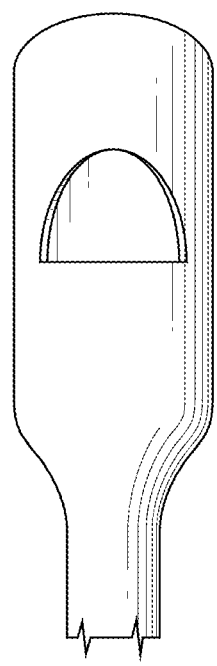
FIGS. 11A and 11B are a top view and a side view, respectively, of a cobra work tip with a semicircular cutting gap wherein the major portion of the gap is toward the proximal end of the work tip.
Figure 11A:
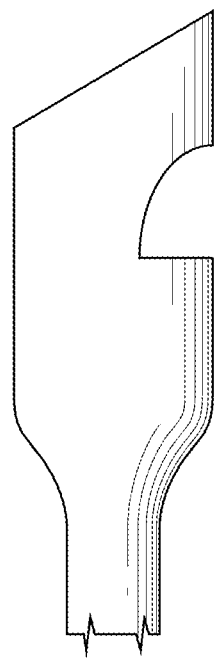

Like FIGS. 9A and 9B, FIGS. 10A and 10B are a bottom view and a side view, respectively, of a cobra work tip with a triangular cutting gap. As shown in FIG. 10B the shape of the distal edge of the gap is perpendicular to the outer surface and the rest falls along a straight line that extends in the proximal direction toward the outer surface. The portion of the edge that reaches the outer surface at the distal location in FIG. 10B would typically engage in cutting the cataract It should be noted that vibration of the work tip in any of the foregoing designs causes both the distal and proximal edges of the gap 154 to have ultrasonic force. Therefore, however the surgeon manipulates the tip, so long as an edge comes into contact with the tissue, it will cut. The greatest force will likely be from a perpendicular edge in side view as opposed to a curved or angled edge. Further, while in a preferred embodiment the cutting gap is provided at the bottom of the cobra work tip as shown in FIG. 5, additional cutting can be achieved when it is at a side or top location. In particular, FIG. 11A shows a cutting gap similar to that in FIG. 7A but located on the top of the cobra work tip as opposed to the bottom, where the "top" is defined as the location of the most proximal area of the edge 155 (See FIG. 4A). FIG. 11B is a side view of the cutting gap located on the top of the cobra tip. Whenever the gap is brought into contact with tissue as the surgeon manipulates the handpiece, regardless of where the gap is located on the work tip, there will be some cutting.

With the cost savings from (a) eliminating the threaded connection between the connecting body and work tip; (b) eliminating the need to form an irrigation fluid channel through the handpiece; and (c) eliminating the need to provide water and corrosion protection for the housing and power cord, the cost of the hand piece can be sufficiently low that it can be a disposable single-use item.

Even more savings can be realized by making the housing with at least part of an electrical terminal or socket such that the power cord can be plugged and unplugged from the socket of the housing. Thus, power cord need not be disposed of and can be reused without sterilization.

While the invention has been shown and described in connection with the removal of a cataract from the eye of a patient, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. An ultrasonic surgical handpiece comprising:
   a transducer having a distal end and a lumen;
   a connecting body attached to said transducer distal end;
   a tube with a proximal end attached to and surrounded by the connecting body and a work tip attached to a distal end of the tube;
   a housing with a large diameter proximal portion for containing the connecting body, the transducer and a portion of the tube, said housing having a reduced diameter distal portion and being formed without provisions for water proofing;
   an aspiration fluid channel that extends through the work tip, the tube, the connecting body and the transducer, and exits the housing at a proximal end thereof;
   an irrigation fluid line that extends between an inner surface of the reduced diameter distal portion of the housing and the tube starting from the vicinity of the work tip and exiting at the reduced diameter distal portion of the housing at a location distal of the connecting body;
   wherein said tube extends from the proximal portion of the housing, through the lumen of the transducer and through the connecting body; and
   whereby the lack of provisions for water proofing causes the handpiece to be reduced in cost and disposable.

2. The ultrasonic surgical handpiece according to claim 1 wherein said housing is in the form of a main housing section from which the irrigation fluid line exits and a connected distal housing section, wherein the distal section is a flexible sleeve located distally of the main housing section.

3. The ultrasonic surgical handpiece according to claim 2 wherein the sleeve is made of silicone and the main housing section is made with a rigid structure.

4. The ultrasonic surgical handpiece according to claim 1 further comprising a power cord for providing an ultrasonic signal to said transducer, said power cord being detachably connected to said housing and the transducer therein, said power cord being formed without provisions for water proofing or corrosion resistance.

5. The ultrasonic surgical handpiece according to claim 4 further comprising: a socket with connectors, said socket being located at a proximal end of the transducer and said connectors of the socket being electrically attached to the transducer, said socket further being attached to the proximal end of the housing; and wherein the connectors of the socket are adapted to be electrically connected to and disconnected from the power cord.

6. The ultrasonic surgical handpiece according to claim 1 wherein the work tip is a cobra tip in the form of a tube with a first portion of a certain diameter, a second portion expanded in a cone shape followed by a third portion of an expanded diameter, said cobra tip having a distal opening slanted in the distal to the proximal direction with respect to an axis thereof; and wherein said cobra tip further includes a cutting gap in a side wall of the expanded diameter portion, said cutting gap extending both perpendicular to the axial direction and in the axial direction of the cobra tip sufficient for an edge thereof to engage tissue.

7. The ultrasonic surgical handpiece according to claim 6 wherein said cutting gap is located in a bottom region of the cobra tip adjacent a most proximal edge of the cobra tip slanted opening.

8. The ultrasonic surgical handpiece according to claim 6 wherein said cutting gap is located in a top region of the cobra tip adjacent the most distal edge of the cobra tip slanted opening.

9. An ultrasonic surgical handpiece comprising
a transducer;
a connecting body attached to said transducer;
a tubular work tip attached to the connecting body;
a housing for containing the connecting body, the transducer and a portion of the tubular work tip, said housing being formed without provisions for water proofing;
an aspiration fluid channel that extends through the work tip, the connecting body and the transducer, and exits the housing at a proximal end thereof;
an irrigation fluid line that extends between an inner surface of the housing and the tubular work tip and exits the housing distal of the connecting body;
a power cord with a plug for providing an ultrasonic signal, a sterile sheet, an electrical socket attached in said housing and connected to said transducer;
wherein the plug of said power cord and said socket have attachable and detachable mating pins and openings, said sterile sheet is located between said plug and socket and being penetrated by the pins when said pins and openings are attached; and
wherein the handpiece is so adapted to be reduced in cost and disposable.

10. A work tip for an ultrasonic surgical handpiece comprising;

a cobra tip in the form of a tube having a wall and a lumen extending therethrough, wherein the tube has a first portion of a certain diameter, a second portion expanded in a cone shape and having a distal end, followed by a third portion of an expanded diameter, said cobra tip having a distal opening slanted in the distal to the proximal direction with respect to an axis thereof;
wherein said cobra tip further includes a cutting gap in a side wall of the expanded diameter portion proximal the distal end,
wherein said cutting gap extends through the wall and enters the lumen;
and wherein said cutting gap extending both perpendicular to the axial direction and in the axial direction of the cobra tip sufficient for an edge thereof to engage tissue.

11. The work tip for an ultrasonic surgical handpiece according to claim 10 wherein said cutting gap is located in a bottom region of the cobra tip adjacent a most proximal edge of the cobra tip slanted opening.

12. The work tip for an ultrasonic surgical handpiece according to claim 10 wherein the first and third portions have cylindrical shapes.

13. The work tip for an ultrasonic surgical handpiece according to claim 10 wherein said cutting gap has a semicircular shape in plan view with a major portion toward a distal end of the work tip, and in side view an edge at its major portion is generally perpendicular to a central axis of the work tip and the more proximal edges are a curve that extends toward an outer surface.

14. The work tip for an ultrasonic surgical handpiece according to claim 10 wherein said cutting gap has a semicircular shape in plan view with a major portion toward a proximal end of the work tip, and in side view an edge at its major portion is generally perpendicular to a central axis of the work tip and the more distal edges are a curve that extends toward an outer surface.

15. The work tip for an ultrasonic surgical handpiece according to claim 10 wherein said cutting gap has an oval shape in plan view with a major axis transverse to an axis of the work tip, and in side view the cutting gap has an inverted U shape.

16. The work tip for an ultrasonic surgical handpiece according to claim 10 wherein said cutting gap has a triangular shape in plan view with a base portion toward a distal end of the work tip, and in side view a distal edge is generally perpendicular to a central axis of the work tip and more proximal edges are along a straight line that extends toward an outer surface.

17. The work tip for an ultrasonic surgical handpiece according to claim 10 wherein said cutting gap has a triangular shape in plan view with a base portion toward a proximal end of the work tip, and in side view a proximal edge is generally perpendicular to a central axis of the work tip and more distal edges are along a straight line that extends toward an outer surface.

18. An ultrasonic surgical handpiece comprising:
a transducer having a distal end and a lumen;
a connecting body attached to said transducer distal end;
a tubular work tip;
a tube with a proximal end attached to and surrounded by the connecting body and a distal end attached to the tubular work tip;
a rigid housing for containing the connecting body, the transducer and a portion of the tube;

an aspiration fluid channel that extends through the work tip, the connecting body and the transducer, and exits the housing at a proximal end thereof;
a flexible tubular sleeve fastened to a distal end of the rigid housing and extending to a position just short of the tubular work tip;
a connector for an irrigation fluid line located toward the distal end of the rigid housing,
wherein said tube extends from the proximal end of the housing, through the lumen of the transducer and through the connecting body;
whereby an irrigation fluid channel extends between an inner surface of the flexible sleeve and the tube, and exits at the tubular work tip.

19. The ultrasonic surgical handpiece according to claim 18 wherein the tubular work tip is a cobra tip.

20. The ultrasonic surgical handpiece according to claim 19 wherein the cobra tip includes a cutting gap in a side wall of an expanded diameter portion thereof.

21. The ultrasonic surgical handpiece according to claim 19 wherein the rigid housing has a particular diameter to contain the transducer and a portion of the connecting body, and a reduced diameter portion to contain another portion of the connecting body, the tube and the connector for the irrigation fluid line.

22. The ultrasonic surgical handpiece according to claim 21 wherein the tube is a continuous piece from the tubular work tip to a proximal end of the handpiece and forms the aspiration fluid channel through the connecting body and transducer and wherein the rigid housing is in the form of two axial halves placed about the transducer and the connecting body, and sealed.

23. The ultrasonic surgical handpiece according to claim 21 wherein the tube is a plurality of sections connected together.

24. The ultrasonic surgical handpiece according to claim 19 wherein the flexible sleeve is made of silicone.

25. An ultrasonic surgical handpiece comprising:
a transducer having a distal end and a lumen;
a connecting body attached to said transducer distal end;
a tube with a proximal end attached to and surrounded by the connecting body and a work tip attached to a distal end of the tube;
a housing with a large diameter proximal portion for containing the connecting body and a reduced diameter distal portion;
an aspiration fluid channel that extends through the work tip, the tube, the connecting body and the transducer, and exits the housing at a proximal end thereof;
an irrigation fluid line that extends between an inner surface of the reduced diameter distal portion of the housing and the tube starting from the vicinity of the work tip and existing the reduced diameter distal portion of the housing at a location distal of the connecting body; and
a power cord for providing an ultrasonic signal to said transducer, said power cord being detachably connected to said housing and the transducer therein; and
wherein said tube extends from the proximal end of the housing, through the lumen of the transducer and through the connecting body.

26. The ultrasonic surgical handpiece according to claim 25 further comprising: a socket with connectors, said socket being located at a proximal end of the transducer and said connectors of the socket being electrically attached to the transducer, said socket further being attached to the proximal end of the housing; and wherein the connectors of the socket are adapted to be electrically connected to and disconnected from the power cord.

* * * * *